United States Patent
Bobeck et al.

(10) Patent No.: US 9,834,487 B2
(45) Date of Patent: Dec. 5, 2017

(54) HIGHLY CONCENTRATED PHOSPHORIC OR THIOPHOSPHORIC TRIAMIDE FORMULATION

(71) Applicant: Koch Agronomic Services, LLC, Wichita, KS (US)

(72) Inventors: Drew R. Bobeck, Doraville, GA (US); Kwame Owusu-Adom, Grayson, GA (US)

(73) Assignee: Koch Agronomic Services, LLC, Wichita, KS (US)

( * ) Notice: Subject to any disclaimer, the term of this patent is extended or adjusted under 35 U.S.C. 154(b) by 30 days.

(21) Appl. No.: 15/206,657

(22) Filed: Jul. 11, 2016

(65) Prior Publication Data

US 2017/0015604 A1    Jan. 19, 2017

Related U.S. Application Data

(60) Provisional application No. 62/191,838, filed on Jul. 13, 2015.

(51) Int. Cl.
*C05G 3/08* (2006.01)
*C07F 9/22* (2006.01)
*C05C 9/00* (2006.01)

(52) U.S. Cl.
CPC ............... *C05G 3/08* (2013.01); *C05C 9/00* (2013.01); *C07F 9/224* (2013.01)

(58) Field of Classification Search
CPC .................................. C05G 3/08; C05C 9/00
See application file for complete search history.

(56) References Cited

U.S. PATENT DOCUMENTS

| | | |
|---|---|---|
| 5,352,265 A | 10/1994 | Weston et al. |
| 5,364,438 A | 11/1994 | Weston et al. |
| 5,698,003 A | 12/1997 | Omilinsky et al. |
| 8,048,189 B2 | 11/2011 | Whitehurst et al. |
| 8,163,058 B2 | 4/2012 | Whitehurst et al. |
| 8,430,942 B2 | 4/2013 | Urrutia et al. |
| 8,603,211 B2 | 12/2013 | Rahn et al. |
| 8,617,425 B2 | 12/2013 | Cigler |
| 8,888,886 B1 | 11/2014 | Whitehurst et al. |
| 9,034,072 B2 | 5/2015 | Gabrielson et al. |
| 9,056,804 B2 | 6/2015 | Phillip et al. |
| 9,090,516 B2 | 7/2015 | Roberts |
| 9,096,476 B2 | 8/2015 | Roberts |
| 9,266,789 B2 | 2/2016 | Ortiz-Suarez et al. |
| 2009/0035384 A1 | 2/2009 | Lambeth et al. |
| 2013/0145806 A1 | 6/2013 | Iannotta et al. |
| 2014/0037570 A1 | 2/2014 | Whitehurst et al. |
| 2014/0047884 A1* | 2/2014 | Gabrielson ............ C05B 15/00 71/28 |
| 2015/0143860 A1 | 5/2015 | McKnight et al. |
| 2015/0197460 A1 | 7/2015 | Gabrielson et al. |
| 2015/0218060 A1 | 8/2015 | Hayes |
| 2015/0307407 A1 | 10/2015 | Sutton et al. |
| 2015/0315092 A1* | 11/2015 | McKnight ............... C05G 3/08 71/27 |
| 2016/0046534 A1 | 2/2016 | Dietrich et al. |
| 2016/0050938 A1 | 2/2016 | Jenkins |
| 2016/0052833 A1 | 2/2016 | Gabrielson et al. |
| 2016/0060184 A1 | 3/2016 | Gabrielson et al. |
| 2016/0075609 A1 | 3/2016 | Gabrielson et al. |
| 2016/0075613 A1 | 3/2016 | Gabrielson et al. |
| 2016/0107947 A1 | 4/2016 | McKnight et al. |
| 2016/0159707 A1 | 6/2016 | Waliwitiya |

FOREIGN PATENT DOCUMENTS

| | | |
|---|---|---|
| BR | PI0904949 | 6/2011 |
| CN | 101525348 A | 9/2009 |
| CN | 103833471 B | 8/2015 |
| CN | 103755484 B | 2/2016 |
| DE | 102013012760 A1 | 10/2014 |
| EP | 1851183 B1 | 7/2015 |
| EP | 2986108 A2 | 2/2016 |
| WO | 2008000196 A1 | 1/2008 |
| WO | 2010072184 A2 | 7/2010 |
| WO | 2013090324 A1 | 6/2013 |
| WO | 2014055132 A1 | 4/2014 |
| WO | 2015001391 A1 | 1/2015 |
| WO | 2015001457 A2 | 1/2015 |
| WO | 2016022582 A1 | 2/2016 |
| WO | 2016054012 A1 | 4/2016 |
| WO | 2016103168 A1 | 6/2016 |

OTHER PUBLICATIONS

International Search Report and Written Opinion received for PCT Patent Application No. PCT/US2016/041769, dated Oct. 6, 2016, 10 pages.

* cited by examiner

*Primary Examiner* — Jennifer A Smith

(57) ABSTRACT

The present disclosure relates to a novel highly concentrated phosphoric or thiophosphoric triamide formulation with enhanced stability against crystallization or freezing under extended exposure to low temperature of 0° C. or below. It also provides a method to make and use such formulations.

13 Claims, No Drawings

HIGHLY CONCENTRATED PHOSPHORIC OR THIOPHOSPHORIC TRIAMIDE FORMULATION

RELATED APPLICATION

This application claims the benefit of U.S. Provisional Application No. 62/191,838 filed on Jul. 13, 2015, which is incorporated by reference in its entirety.

TECHNICAL FIELD

The present disclosure relates to a novel highly concentrated phosphoric or thiophosphoric triamide liquid formulation with enhanced stability against crystallization or freezing under extended exposure to low temperatures of 0° C. or below, and methods to make and use such a formulation.

BACKGROUND

Nitrogen loss due to ammonia volatilization occurs with urea or urea-based fertilizers, in part, because of rapid hydrolysis of urea on or near the soil surface by microbially generated urease enzymes. A urease inhibitor such as a phosphoric triamide or thiophosphoric triamide (particularly N-(n-butyl) thiophosphoric triamide, NBPT) can slow down the enzymatic breakdown of urea by inhibition of the urease enzyme. This provides an effective means of managing losses of nitrogen in the form of ammonia from surface-applied urea containing fertilizers.

A phosphoric triamide or thiophosphoric triamide such as NBPT as a urease inhibitor can be applied onto a granular fertilizer formulation by first blending a concentrated solution of the phosphoric triamide or thiophosphoric triamide that is dissolved in a solvent such as a glycol or glycol derivative or a mixed solvent of a glycol or glycol derivative and a liquid amide (See U.S. Pat. No. 5,698,003). Alternatively, a phosphoric triamide or thiophosphoric triamide urease inhibitor such as NBPT can be introduced into a urea melt to form an incorporated urea fertilizer (See WO 2015/027244). In addition, a highly concentrated dry formulation of NBPT such as AGROTAIN® DRI-MAXX nitrogen stabilizer, which can adhere to the urea granules without adding additional moisture to the blend, can be used to treat urea granules to make a NBPT-containing urea as well (See U.S. Pat. No. 9,034,072).

Industrial grade N-(n-butyl)thiophosphoric triamide (NBPT) is a waxy-like solid compound, which is not easy to use directly and which is also sensitive to moisture and elevated temperature. The use of a liquid formulation of NBPT is thus highly desirable because it greatly facilitates the introduction of the NBPT onto granular urea and into liquid fertilizers containing urea. Suitable solvents to prepare NBPT solutions should comply with some basic requirements such as high solubility and stability of NBPT in the solvent, resistance of the resulting NBPT solutions against crystallization or freezing at a low temperature, low viscosity of the concentrated solutions of NBPT, low toxicity, volatility and flammability, minimum content of water in the commercially available form of the solvent, and low cost.

OBJECTIVES AND SUMMARY OF THE INVENTION

One of the primary objectives of the present disclosure is to provide a highly concentrated liquid phosphoric or thiophosphoric triamide formulation that is resistant to crystallization or freezing under extended exposure to a low temperature of 0° C. or below.

Although the prior art discloses that solutions with a high concentration of NBPT can be prepared and be reasonably stable under ambient temperature (See U.S. Pat. No. 5,698,003), it is well-known that such a highly concentrated NBPT solution is often not recommended to be stored at 0° C. or below over an extended period of time due to the likelihood of the solution freezing or crystallizing. "If the product is subjected to temperatures below 32° F. (0° C.) for an extended period of time, it will become gel-like and the formation of crystals will result in the bottom of the container". (See AGROTAIN® ULTRA Product Information: http://ekova.com/download/product-information/Agrotain_Ultra/Agrotain%20ultra%20Label.pdf).

The higher the concentration of NBPT in a solution, the more likely the whole solution will become frozen and/or the more likely the NBPT will precipitate out from the solution at or below 0° C. In addition, the more impurities in the NBPT, the more likely a solution with a high concentration of NBPT may freeze more quickly at or below 0° C.

AGROTAIN® ULTRA is a liquid formulation of NBPT with the highest known NBPT concentration of 26.7% by weight. The product is known to precipitate or become a gel if it is subjected to temperatures at or below 0° C. for an extended period of time as mentioned in the product information. Although expired U.S. Pat. No. 5,698,003, which is the patent that covers AGROTAIN® ULTRA, discloses that the solvent system could be helpful at low temperatures for flowability, it is silent on the freezing or crystallization issues at low temperature. In addition, the highest NBPT concentration in all the exemplified formulations of the '003 patent is only about 25%, which is even lower than the NBPT concentration of AGROTAIN® ULTRA. Actually, Column 8, lines 18-19 of the 003 patent refers to "concentrated solutions normally containing 25 percent by weight". The solvent systems disclosed in U.S. Pat. No. 5,698,003 will not help for a highly concentrated NBPT solution with a concentration of at least 35% by weight as disclosed in the present disclosure.

In addition, the commercial NBPT solutions sometimes may include a dye (or a colorant) because of the requirement to provide product differentiation. Many dyes used in NBPT solutions are very soluble in water but much less soluble in organic solvents, especially at lower temperatures. Thus, the added dye may hinder efforts to make a lower temperature-resistant, highly concentrated NBPT solution. Further, the higher the concentration of dye, the more difficult it is to achieve a lower temperature-resistant, highly concentrated NBPT solution.

In some industrial applications, such as making NBPT incorporated urea granules, it is highly desirable to use very concentrated NBPT solutions to mix with molten urea. The high concentration alleviates transportation, storage, environmental, and handling issues. However, due to the physical stability disadvantages at lower temperature for highly concentrated NBPT solutions as discussed, so far, there is no commercially available liquid NBPT formulation with a concentration of at least 35% by weight that can withstand extended periods of exposure to temperature at 0° C. or below.

The present disclosure provides a highly concentrated formulation with a phosphoric or thiophosphoric triamide concentration of at least 35% by weight that can withstand extended exposure to lower temperatures at 0° C. or below, and methods to make and use such a formulation.

In one embodiment, the present disclosure provides a highly concentrated phosphoric or thiophosphoric triamide composition comprising:
 i). a phosphoric or thiophosphoric triamide with a concentration range from 35% to about 50% by weight, wherein said phosphoric or thiophosphoric triamide is a compound according to Formula I:

(X=P)(NH$_2$)$_2$NR$^1$R$^2$   (Formula I)

wherein X is oxygen or sulfur, and R$^1$ and R$^2$ are independently hydrogen, C$_1$-C$_{12}$ alkyl, C$_3$-C$_{12}$ cycloalkyl, C$_6$-C$_{14}$ aryl, C$_2$-C$_{12}$ alkenyl, C$_2$-C$_{12}$ alkynyl, C$_5$-C$_{14}$ heteroaryl, C$_1$-C$_{14}$ heteroalkyl, C$_2$-C$_{14}$ heteroalkenyl, C$_2$-C$_{14}$ heteroalkynyl, or C$_3$-C$_{12}$ cycloheteroalkyl;
 ii). a glycol or glycol derivative with a concentration range from about 5% to about 30% by weight, wherein said glycol is a compound according to C$_n$H$_{2n}$(OH)$_2$ (Formula II), and n is 2-12.
 iii). a liquid amide with a concentration range from about 25% to about 65% by weight, wherein said liquid amide is selected from the group consisting of 2-pyrrolidone, N—(C$_1$-C$_{12}$ alkyl)-2-pyrrolidone, and an amide with the formula R$^1$CONR$^2$R$^3$, wherein R$^1$ is a hydrogen or a C$_1$-C$_4$ alkyl group, and R$^2$ and R$^3$ are independently hydrogen or C$_1$-C$_{12}$ alkyl group.

In another embodiment, the present disclosure provides a highly concentrated phosphoric or thiophosphoric triamide composition comprising:
 i). a phosphoric or thiophosphoric triamide with a concentration range from 35% to about 50% by weight, wherein said phosphoric or thiophosphoric triamide is a compound according to Formula I:

(X=P)(NH$_2$)$_2$NR$^1$R$^2$   (Formula I)

wherein X is oxygen or sulfur, and R$^1$ and R$^2$ are independently hydrogen, C$_1$-C$_{12}$ alkyl, C$_3$-C$_{12}$ cycloalkyl, C$_6$-C$_{14}$ aryl, C$_2$-C$_{12}$ alkenyl, C$_2$-C$_{12}$ alkynyl, C$_5$-C$_{14}$ heteroaryl, C$_1$-C$_{14}$ heteroalkyl, C$_2$-C$_{14}$ heteroalkenyl, C$_2$-C$_{14}$ heteroalkynyl, or C$_3$-C$_{12}$ cycloheteroalkyl;
 ii). a glycol or glycol derivative with a concentration range from about 5% to about 30% by weight, wherein said glycol is a compound according to C$_n$H$_{2n}$(OH)$_2$ (Formula II), and n is 2-12.
 iii). a liquid amide with a concentration range from about 25% to about 65% by weight, wherein said liquid amide is selected from the group consisting of 2-pyrrolidone, N—(C$_1$-C$_{12}$ alkyl)-2-pyrrolidone, and an amide with the formula R$^1$CONR$^2$R$^3$, wherein R$^1$ is a hydrogen or a C$_1$-C$_4$ alkyl group, and R$^2$ and R$^3$ are independently hydrogen or C$_1$-C$_{12}$ alkyl group; and
 iv). a dye with a concentration range from about 1.0% to about 2.0% by weight.

In one further embodiment, the present disclosure provides a highly concentrated phosphoric or thiophosphoric triamide composition comprising:
 i). N-(n-butyl) thiophosphoric triamide (NBPT) with a concentration in the range from about 40% to about 48% by weight;
 ii). propylene glycol (PG) with a concentration in the range from about 8% to about 20% by weight;
 iii). N-methyl-2-pyrrolidone (NMP) with a concentration in the range from about 35% to about 50% by weight; and
 iv). a dye with a concentration in the range from about 1.2% to about 1.8% by weight.

In another embodiment, the present disclosure provides a method comprising contacting a highly concentrated phosphoric or thiophosphoric triamide composition of the present disclosure with a urea-based fertilizer.

In one embodiment, the present disclosure provides a method of making a highly concentrated NBPT composition by combining NBPT, PG, NMP and a dye to make a homogeneous solution.

In one embodiment, the present disclosure provides a method to make an incorporated urea-containing fertilizer by adding a highly concentrated phosphoric or thiophosphoric triamide composition into a molten urea-containing fertilizer.

DETAILED DESCRIPTION OF THE INVENTION

Phosphoric or thiophosphoric triamides in the present disclosure are compounds according to Formula I:

(X=P)(NH$_2$)$_2$NR$^1$R$^2$   (Formula I)

wherein X is oxygen or sulfur, and R$^1$ and R$^2$ are independently hydrogen, C$_1$-C$_{12}$ alkyl, C$_3$-C$_{12}$ cycloalkyl, C$_6$-C$_{14}$ aryl, C$_2$-C$_{12}$ alkenyl, C$_2$-C$_{12}$ alkynyl, C$_5$-C$_{14}$ heteroaryl, C$_1$-C$_{14}$ heteroalkyl, C$_2$-C$_{14}$ heteroalkenyl, C$_2$-C$_{14}$ heteroalkynyl, or C$_3$-C$_{12}$ cycloheteroalkyl.

X is preferably sulfur.

Preferably, R$^1$ and R$^2$ are independently hydrogen or C$_1$-C$_6$ alkyl.

A preferred phosphoric or thiophosphoric triamide in the present disclosure is a compound according to Formula I, wherein X is sulfur, R$^1$ and R$^2$ are independently hydrogen or C$_1$-C$_6$ alkyl.

The most preferred phosphoric or thiophosphoric triamide in the present disclosure is N-(n-butyl) thiophosphoric triamide (NBPT).

The concentration of the phosphoric or thiophosphoric triamide in the present disclosure is in a range from 35% to about 50% by weight, from about 40% to about 48% by weight. A more preferred concentration range is from about 45% to about 48% by weight.

Glycols in the present disclosure are compounds according to Formula II:

C$_n$H$_{2n}$(OH)$_2$   (Formula II)

wherein n is 2 to 12.
A preferred n is 2 to 6.
A more preferred n is 3.
Preferred glycols in the present disclosure are compounds according to Formula II, wherein n is 2 to 6.
The most preferred glycol in the present disclosure is 1,2-propylene glycol (PG).

Examples of glycols suitable in the present disclosure include but are not limited to ethylene glycol (glycol), propylene glycol (1,2-propanediol), 1,4-butanediol, 1,5-pentanediol, 1,6-hexanediol, 1,10-decanediol, 1,7-heptanediol, 1,9-nonanediol, 1,8-octanediol, 1,3-propanediol, 1,3-butanediol, 1,4-butanediol, 2,3-butanediol, 2,4-pentauediol, 2,5-hexanediol, 4,5-octanediol, 3,4-hexanediol, and any combination thereof.

Examples of glycol derivatives suitable in the present disclosure may include but are not limited to ethylene glycol monostearate, ethylene glycol distearate, ethylene glycol amido stearate, propylene glycol monostearate, propylene glycol dicaprylate, propylene glycol dicaprate diacetate glycol, dilaurate glycol, dipalmite glycol, diformate glycol, dibutyrate glycol, dibenzorate glycol, dipalmate glycol, dipropionate glycol, monoacetate glycol, monopalmitate glycol, monoformate glycol, diethylene glycol monostearate, and any combination thereof.

Glycol derivatives in the present disclosure may also include $C_3$-$C_{12}$ triols and/or $C_3$-$C_{12}$ triol derivatives, including $C_3$-$C_6$ triols. The most preferred triol in the present disclosure is glycerol. Examples of triol derivatives include but are not limited to glycerol monostearate, glycerol distearate, glycerol monooleate, glycerol monolaurate, glycerol dilaurate, glycerol dipalmitate, glycerol monopalmitate, glycerol triacetate, glycerol tribenzoate, glycerol tributyrate, glycerol trimyristate, glycerol trioleate, glycerol trilaurate, glycerol tripalmitate glycerol tristearate, and any combination thereof.

The total concentration of glycols and/or glycol derivatives in the present disclosure is in the range from about 5% to about 30% by weight. The preferred concentration range is from about 8% to about 20% by weight. The more preferred concentration range is from about 10% to about 15% by weight.

Liquid amides in the present disclosure include but are not limited to:
2-pyrrolidone;
N—($C_1$-$C_{12}$ alkyl)-2-pyrrolidone; and
an amide with the formula $R^1CONR^2R^3$, wherein $R^1$ is a hydrogen or a $C_1$-$C_4$ alkyl group, and $R^2$ and $R^3$ are independently hydrogen or $C_1$-$C_{12}$ alkyl group.

The preferred liquid amide in the present disclosure is N—($C_1$-$C_{12}$ alkyl)-2-pyrrolidone.

The most preferred liquid amide in the present disclosure is N-methyl-2-pyrrolidone (NMP).

The total concentration range of a liquid amide in the present disclosure is in a range from about 25% to about 65% by weight, including from about 30% to about 60% by weight and from about 35% to about 60% by weight. A preferred concentration range is from about 35% to about 50% by weight.

A dye may also be included in a highly concentrated phosphoric or thiophosphoric triamide formulation in the present disclosure. Any commonly used dye including food dyes may be used to provide visual evidence of the uniformity of the distribution of the components of formulations containing phosphoric or thiophosphoric triamide and dye.

Examples of dyes suitable in the present disclosure include but are not limited to FD&C Blue No. 1, FD&C Blue No. 1, FD&C Green No. 3, FD&C Yellow No. 5, FD&C Red No. 3, FD&C Red No. 40, FD&C Yellow No. 6, and AGROTAIN® ULTRA green dye, or a combination thereof.

The amount of dye added in the present disclosure may have substantial impact to the cold weather resistance or crystallization. A higher concentration of dye may be needed in a highly concentrated phosphoric or thiophosphoric triamide formulation to achieve the required level of color. However, a dye with very high concentration may expedite crystallization of NBPT or freezing of the whole solution at lower temperatures.

The weight percentage range of a dye in a highly concentrated phosphoric or thiophosphoric triamide formulation in the present disclosure may be from 0.1% to 5%, 0.5% to 5%, 1% to 5%, 2% to 5%, 3% to 5%, 4% to 5%, 0.1% to 4%, 0.5% to 4%, 1% to 4%, 2% to 4%, 3% to 4%, 0.1% to 3%, 0.5% to 3%, 1% to 3%, 2% to 3%, 0.1% to 2%, 0.5% to 2%, 1% to 2% by weight. A more preferred concentration weight percentage range is from about 1.2% to about 1.8% by weight.

A highly concentrated phosphoric or thiophosphoric triamide formulation in the present disclosure may contain one or more ($C_1$-$C_{16}$ alkyl) ($C_5$-$C_6$ aryl) polyether alcohols as surfactants such as octylphenol polyether alcohol. The total weight percentage range of the ($C_1$-$C_{16}$ alkyl) ($C_5$-$C_6$ aryl) polyether alcohols in the highly concentrated phosphoric or thiophosphoric triamide formulation in the present disclosure may be from about 1% to about 10% by weight.

A highly concentrated phosphoric or thiophosphoric triamide formulation according to the present disclosure may also contain one or more ($C_5$-$C_6$ aryl) ($C_1$-$C_4$ alkyl) alcohols such as benzyl alcohol. The total weight percentage range of the ($C_5$-$C_6$ aryl) ($C_1$-$C_4$ alkyl) alcohols in the highly concentrated phosphoric or thiophosphoric triamide formulation of the present disclosure may be from about 1% to about 10% by weight.

A highly concentrated phosphoric or thiophosphoric triamide solution in the present disclosure may also contain one or more of the following solvents selected from the group consisting of benzyl alcohol, dimethyl sulfoxide (DMSO), morpholine, and ethoxylated amines, wherein the total weight percentage of such solvent in the highly concentrated phosphoric or thiophosphoric triamide formulation may be from about 1% to about 10% by weight.

In one embodiment, the present disclosure provides a highly concentrated phosphoric or thiophosphoric triamide composition comprising:
i). a phosphoric or thiophosphoric triamide with a concentration range from 35% to about 50% by weight, wherein said phosphoric or thiophosphoric triamide is a compound according to Formula I, wherein X is oxygen or sulfur, and $R^1$ and $R^2$ are independently hydrogen, $C_1$-$C_{12}$ alkyl, $C_3$-$C_{12}$ cycloalkyl, $C_6$-$C_{14}$ aryl, $C_2$-$C_{12}$ alkenyl, $C_2$-$C_{12}$ alkynyl, $C_5$-$C_{14}$ heteroaryl, $C_1$-$C_{14}$heteroalkyl, $C_2$-$C_{14}$ heteroalkenyl, $C_2$-$C_{14}$ heteroalkynyl, or $C_3$-$C_{12}$ cycloheteroalkyl;
ii). a glycol or glycol derivative with a concentration range from about 5% to about 30% by weight, wherein said glycol is a compound according to Formula II, and wherein n is 2-12; and
iii). a liquid amide with a concentration range from about 25% to about 65% by weight, wherein said liquid amide is selected from the group consisting of 2-pyrrolidone, N—($C_1$-$C_{12}$ alkyl)-2-pyrrolidone, or an amide with the formula $R^1CONR^2R^3$, wherein $R^1$ is a hydrogen or a $C_1$-$C_4$ alkyl group, and $R^2$ and $R^3$ are independently hydrogen or $C_1$-$C_{12}$ alkyl group.

In one preferred embodiment, the present disclosure provides a highly concentrated phosphoric or thiophosphoric triamide composition comprising:
i). a phosphoric or thiophosphoric triamide with a concentration range from 35% to about 50% by weight, wherein said phosphoric or thiophosphoric triamide is a compound according to Formula I, wherein X is sulfur, $R^1$ and $R^2$ are independently hydrogen or $C_1$-$C_6$ alkyl;
ii). a glycol or glycol derivative with a concentration range from about 5% to about 30% by weight, wherein said glycol is a compound according to Formula II, and wherein n is 2-12; and
iii). a liquid amide with a concentration range from about 25% to about 65% by weight, wherein said liquid amide is selected from the group consisting of 2-pyrrolidone, N—($C_1$-$C_{12}$ alkyl)-2-pyrrolidone, or an amide with the formula $R^1CONR^2R^3$, wherein $R^1$ is a hydrogen or a $C_1$-$C_4$ alkyl group, and $R^2$ and $R^3$ are independently hydrogen or $C_1$-$C_{12}$ alkyl group.

In a more preferred embodiment, the present disclosure provides a highly concentrated phosphoric or thiophosphoric triamide composition comprising:
  i). N-(n-butyl) thiophosphoric triamide (NBPT) with a concentration range from 35% to about 50% by weight;
  ii). a glycol or glycol derivative with a concentration range from about 5% to about 30% by weight, wherein said glycol is a compound according to Formula II, and wherein n is 2-12; and
  iii). a liquid amide with a concentration range from about 25% to about 65% by weight, wherein said liquid amide is selected from the group consisting of 2-pyrrolidone, N—($C_1$-$C_{12}$ alkyl)-2-pyrrolidone, or an amide with the formula $R^1CONR^2R^3$, wherein $R^1$ is a hydrogen or a $C_1$-$C_4$ alkyl group, and $R_2$ and $R_3$ are independently hydrogen or $C_1$-$C_{12}$ alkyl group.

In another embodiment, the present disclosure provides a highly concentrated phosphoric or thiophosphoric triamide composition comprising:
  i). a phosphoric or thiophosphoric triamide with a concentration range from 35% to about 50% by weight, wherein said phosphoric or thiophosphoric triamide is a compound according to Formula I, wherein X is oxygen or sulfur, and $R^1$ and $R^2$ are independently hydrogen, $C_1$-$C_{12}$ alkyl, $C_3$-$C_{12}$ cycloalkyl, $C_6$-$C_{14}$ aryl, $C_2$-$C_{12}$ alkenyl, $C_2$-$C_{12}$ alkynyl, $C_5$-$C_{14}$ heteroaryl, $C_1$-$C_{14}$ heteroalkyl, $C_2$-$C_{14}$ heteroalkenyl, $C_2$-$C_{14}$ heteroalkynyl, or $C_3$-$C_{12}$ cycloheteroalkyl;
  ii). a glycol or glycol derivative with a concentration range from about 5% to about 30% by weight, wherein said glycol is a compound according to Formula II, and wherein n is 2-12;
  iii). a liquid amide with a concentration range from about 25% to about 65% by weight, wherein said liquid amide is selected from the group consisting of 2-pyrrolidone, N—($C_1$-$C_{12}$ alkyl)-2-pyrrolidone, and an amide with the formula $R^1CONR^2R^3$, wherein $R^1$ is a hydrogen or a $C_1$-$C_4$ alkyl group, and $R^2$ and $R^3$ are independently hydrogen or $C_1$-$C_{12}$ alkyl group; and
  iv). a dye with a concentration range from about 1.0% to about 2.0% by weight.

In another preferred embodiment, the present disclosure provides a highly concentrated phosphoric or thiophosphoric triamide composition comprising:
  i). a phosphoric or thiophosphoric triamide with a concentration range from 35% to about 50% by weight, wherein said phosphoric or thiophosphoric triamide is a compound according to Formula I, wherein X is sulfur, $R^1$ and $R^2$ are independently hydrogen or $C_1$-$C_6$ alkyl;
  ii). a glycol or glycol derivative with a concentration range from about 5% to about 30% by weight, wherein said glycol is a compound according to Formula II, and wherein n is 2-12;
  iii). a liquid amide with a concentration range from about 25% to about 65% by weight, wherein said liquid amide is selected from the group consisting of 2-pyrrolidone, N—($C_1$-$C_{12}$ alkyl)-2-pyrrolidone, and an amide with the formula $R^1CONR^2R^3$, wherein $R^1$ is a hydrogen or a $C_1$-$C_4$ alkyl group, and $R^2$ and $R^3$ are independently hydrogen or $C_1$-$C_{12}$ alkyl group; and
  iv). a dye with a concentration range from about 1.0% to about 2.0% by weight.

In another more preferred embodiment, the present disclosure provides a highly concentrated phosphoric or thiophosphoric triamide composition comprising:
  i). N-(n-butyl) thiophosphoric triamide (NBPT) with a concentration range from 35% to about 50% by weight;
  ii). a glycol or glycol derivative with a concentration range from about 5% to about 30% by weight, wherein said glycol is a compound according to Formula II, and wherein n is 2-12;
  iii). a liquid amide with a concentration range from about 25% to about 65% by weight, wherein said liquid amide is selected from the group consisting of 2-pyrrolidone, N—($C_1$-$C_{12}$ alkyl)-2-pyrrolidone, and an amide with the formula $R^1CONR^2R^3$, wherein $R^1$ is a hydrogen or a $C_1$-$C_4$ alkyl group, and $R^2$ and $R^3$ are independently hydrogen or $C_1$-$C_{12}$ alkyl group; and
  iv). a dye with a concentration range from about 1.0% to about 2.0% by weight.

In one embodiment in the present disclosure, a preferred glycol is a compound according to Formula II, wherein n is 2-6.

In one embodiment in the present disclosure, a more preferred glycol is a compound according to Formula II, wherein n is 3.

In one embodiment in the present disclosure, a glycol can be one or more compounds selected from ethylene glycol, propylene glycol (1,2-propanediol), 1,4-butanediol, 1,5-pentanediol, 1,6-hexanediol, 1,10-decanediol, 1,7-heptanediol, 1,9-nonanediol, 1,8-octanediol, 1,3-propanediol, 1,3-butanediol, 1,4-butanediol, 2,3-butanediol, 2,4-pentanediol, 2,5-hexanediol, 4,5-octanediol, and 3,4-hexanediol.

In one embodiment in the present disclosure, the most preferred glycol is 1,2-propylene glycol (PG).

In one embodiment in the present disclosure, a preferred liquid amide is an N—($C_1$-$C_{12}$ alkyl)-2-pyrrolidone.

In one embodiment in the present disclosure, a preferred liquid amide is N-methyl-2-pyrrolidone (NMP).

In one embodiment in the present disclosure, a preferred total concentration of the phosphoric or thiophosphoric triamide in the composition is in the range from about 40% to about 48% by weight.

In one embodiment in the present disclosure, a more preferred total concentration of the phosphoric or thiophosphoric triamide in the composition is in the range from about 45% to about 48% by weight.

In one embodiment in the present disclosure, a preferred total concentration of the glycols and/or glycol derivatives in the composition is in the range from about 8% to about 20% by weight.

In one embodiment in the present disclosure, a more preferred total concentration of the glycols and/or glycol derivatives in the composition is in the range from about 10% to about 15% by weight.

In one embodiment in the present disclosure, the weight ratio of NMP to PG is more than 1.0.

In one embodiment in the present disclosure, a preferred total concentration of a dye in the composition may be in the range from about 1.2% to about 1.8% by weight.

In one embodiment in the present disclosure, a highly concentrated phosphoric or thiophosphoric triamide composition further comprises one or more ($C_1$-$C_{16}$ alkyl) ($C_5$-$C_6$ aryl) polyether alcohols as surfactants, such as octylphenol polyether alcohol, and the total concentration range of the ($C_1$-$C_{16}$ alkyl) ($C_5$-$C_6$ aryl) polyether alcohols in the composition may be from about 1% to about 10% by weight.

In one embodiment in the present disclosure, a highly concentrated phosphoric or thiophosphoric triamide composition further comprises one or more ($C_5$-$C_6$ aryl) ($C_1$-$C_4$ alkyl) alcohols such as benzyl alcohol, wherein the total concentration range of the (C$_5$-C$_6$ aryl) (C$_1$-C$_4$ alkyl) alcohols in the composition may be from about 1% to about 10% by weight.

In one embodiment in the present disclosure, a highly concentrated phosphoric or thiophosphoric triamide composition further comprises one or more solvents selected from the group consisting of benzyl alcohol, dimethyl sulfoxide (DMSO), morpholine, and ethoxylated amines, wherein the total concentration range of the additional one or more solvents may be from about 1% to about 10% by weight.

In one embodiment, the present disclosure provides a highly concentrated phosphoric or thiophosphoric triamide composition comprising:
  i). N-(n-butyl) thiophosphoric triamide (NBPT) with a concentration in the range from 35% to about 50% by weight;
  ii). a glycol or glycol derivative with a concentration range from about 5% to about 30% by weight, wherein said glycol is a compound according to Formula II, and wherein n is 2-6; and
  iii). N—(C$_1$-C$_{12}$ alkyl)-2-pyrrolidone with a concentration range from about 25% to about 50% by weight.

In another preferred particular embodiment, the present disclosure provides a highly concentrated phosphoric or thiophosphoric triamide composition comprising:
  i). N-(n-butyl) thiophosphoric triamide (NBPT) with a concentration in the range from 35% to about 50% by weight;
  ii). propylene glycol (PG) with a concentration in the range from about 5% to about 30% by weight; and
  iii). N-methyl-2-pyrrolidone (NMP) with a concentration in the range from about 25% to about 50% by weight.

In another preferred particular embodiment, the present disclosure provides a highly concentrated phosphoric or thiophosphoric triamide composition comprising:
  i). N-(n-butyl) thiophosphoric triamide (NBPT) with a concentration in the range from about 42% to about 48% by weight;
  ii). propylene glycol (PG) with a concentration in the range from about 8% to about 15% by weight; and
  iii). N-methyl-2-pyrrolidone (NMP) with a concentration in the range from about 35% to about 45% by weight.

In one further preferred embodiment, the present disclosure provides a highly concentrated phosphoric or thiophosphoric triamide composition comprising:
  i). N-(n-butyl) thiophosphoric triamide (NBPT) with a concentration in the range from about 35% to about 50% by weight;
  ii). a glycol or glycol derivative with a concentration range from about 5% to about 30% by weight, wherein said glycol is a compound according to C$_n$H$_{2n}$(OH)$_2$ (Formula II), and wherein n is 2-6;
  iii). N—(C$_1$-C$_{12}$ alkyl)-2-pyrrolidone with a concentration in the range from about 25% to about 50% by weight; and
  iv). a dye with a concentration in the range from about 1% to about 2% by weight.

In one preferred embodiment, the present disclosure provides a highly concentrated phosphoric or thiophosphoric triamide composition comprising:
  i). N-(n-butyl) thiophosphoric triamide (NBPT) with a concentration in the range from about 35% to about 50% by weight;
  ii). propylene glycol (PG) with a concentration in the range from about 5% to about 30% by weight;
  iii). N-methyl-2-pyrrolidone (NMP) with a concentration in the range from about 25% to about 50% by weight; and
  iv). a dye with a concentration in the range from about 1% to about 2% by weight.

In one preferred embodiment, the present disclosure provides a highly concentrated phosphoric or thiophosphoric triamide composition comprising:
  i). N-(n-butyl) thiophosphoric triamide (NBPT) with a concentration in the range from about 42% to about 48% by weight;
  ii). propylene glycol (PG) with a concentration in the range from about 8% to about 15% by weight;
  iii). N-methyl-2-pyrrolidone (NMP) with a concentration in the range from about 35% to about 45% by weight; and
  iv). a dye with a concentration in the range from about 1.2% to about 1.8% by weight.

In another embodiment, the present disclosure provides a highly concentrated phosphoric or thiophosphoric triamide composition that is physically stable at a temperature of 0° C. or below, and wherein there is substantially no freezing of the composition or crystallization of any solid for at least 14 days at 0° C. or below.

In another embodiment, the present disclosure provides a highly concentrated NBPT composition that is physically stable at a temperature of 0° C. or below, and wherein there is substantially no freezing of the composition or crystallization of any solid for at least 14 days at 0° C. or below. One such highly concentrated NBPT composition comprises NBPT with a concentration in the range from about 42% to about 48% by weight, PG with a concentration in the range from about 8% to about 15% by weight, NMP with a concentration in the range from about 35% to about 45% by weight, and a dye with a concentration in the range from about 1.2% to about 1.8% by weight.

In one further embodiment, a highly concentrated phosphoric or thiophosphoric triamide composition according to the present disclosure can be applied to solid urea-containing fertilizers, such as coating granular urea, added into molten urea-containing fertilizers to make phosphoric or thiophosphoric triamide incorporated urea-containing fertilizers (as described in WO2015/027244 and U.S. Prov. Appl. No. 62/120,101, both herein incorporated by reference), or added into liquid urea-containing fertilizers.

For example, a highly concentrated phosphoric or thiophosphoric triamide composition according to the present disclosure can be incorporated into a homogenous urea-based fertilizer composition by blending said highly concentrated phosphoric or thiophosphoric triamide composition directly with molten urea at a temperature of about 120° C. to about 150° C. prior to the granulation or prilling of the urea in a conventional urea production facility. Sufficient mixing is employed during this blending step to assure that the highly concentrated phosphoric or thiophosphoric triamide composition is homogeneously distributed throughout the molten urea before the melt cools and solidifies in the subsequent granulation step.

In one embodiment, the present disclosure provides a method of making a highly concentrated NBPT composition by combining NBPT, PG, and NMP to make a homogeneous solution.

In one embodiment, the present disclosure provides a method of making a highly concentrated NBPT composition by combining NBPT, PG, NMP and a dye to make a homogeneous solution.

The term "highly concentrated" means a concentration of at least 35% by weight of NBPT in the present disclosure.

The term "extended exposure to low temperature" means that a composition is exposed to temperatures of 0° C. or lower for at least fourteen days.

The term "temperature of 0° C. or below" means a temperature range from about −15° C. to 0° C.

The term "about" means±5% of a value. For example, a skilled artisan will appreciate that "a range from about 10% to about 20% by weight" will also cover a range of "9.5% to 20.5% by weight".

The term "substantially no freezing of the composition or crystallization" means that less than 5% of the total solution is frozen or less than 5% of total solids crystallize out from solution at a temperature of 0° C. or below.

Example 1

Highly Concentrated NBPT Solution

The Highly Concentrated NBPT Solution (Example 1) can be made by either Preparation Method 1 or Preparation Method 2.

Preparation Method 1:

AGROTAIN® ULTRA green dye (1.67 g), propylene glycol (PG) (10.00 g) and N-methyl-2-pyrrolidone (NMP) (43.30 g) are weighed into a glass jar. A magnetic stir bar is added and the jar is sealed. The jar is transferred to a 35-40° C. water bath where the contents are stirred constantly to dissolve the dye. Once the dye is dissolved, the water bath temperature is reduced to 30-35° C. N-(n-Butyl) thiophosphoric triamide crystals (NBPT) (45.00 g) are added to the dye mixture and the jar is placed in the water bath. The contents are stirred vigorously while heating to dissolve NBPT into a homogenous mixture. The homogeneous mixture is then cooled to ambient temperature (~22° C.) before further evaluation.

Preparation Method 2:

AGROTAIN® ULTRA green dye (1.67 g) and propylene glycol (PG) (10.00 g) are weighed into a glass jar equipped with magnetic stir bar. N-(n-Butyl) thiophosphoric triamide crystals (NBPT) (45.00 g) and N-methyl-2-pyrrolidone (NMP) (43.30 g) are weighed into a separate glass jar equipped with magnetic stir bar. Both jars are sealed. The glass jar with AGROTAIN® ULTRA green dye and propylene glycol (PG) is placed in a water bath with a temperature of about 40° C. The glass jar with N-(n-Butyl)thiophosphoric triamide (NBPT) and N-methyl-2-pyrrolidone (NMP) is also placed in a water bath with a temperature of about 35° C. Both mixtures are stirred constantly while heating until the solids are dissolved to provide a homogeneous solution. The two mixtures are then combined and stirred together to form a homogenous mixture that is free of solid. The resulting formulation is cooled to ambient conditions (about 22° C.) before further evaluation.

Examples 2 to 9 are prepared with essentially the same method as Example 1 with either Preparation Method 1 or Preparation Method 2.

| Example # | NBPT (g) | NMP (g) | PG (g) | Dye (g) | Wt. % of NBPT |
|---|---|---|---|---|---|
| 2 | 48.00 | 40.75 | 10.00 | 1.25 | 48.00% |
| 3 | 45.00 | 43.33 | 10.00 | 1.67 | 45.00% |
| 4 | 43.00 | 42.33 | 13.00 | 1.67 | 43.00% |
| 5 | 43.00 | 48.75 | 7.00 | 1.25 | 43.00% |
| 6 | 43.00 | 48.33 | 7.00 | 1.67 | 43.00% |
| 7 | 43.00 | 42.75 | 13.00 | 1.25 | 43.00% |
| 8 | 43.00 | 45.75 | 10.00 | 1.25 | 43.00% |
| 9 | 45.00 | 44.70 | 10.30 | 0.00 | 45.00% |

Stability Test at 0° C.

The purpose of the stability test at 0° C. is to determine if a highly concentrated NBPT solution in the present disclosure will freeze or if any solid will precipitate from the solution at 0° C. after being stored at 0° C. for at least 14 days.

A highly concentrated NBPT solution (Examples 1-9) in a sealed jar is placed into a freezer that is set to the desired temperature (0° C.). The time when the sample is first placed into the freezing temperature is set to time zero. Samples are monitored daily for solidification by slowly tilting each formulation container to observe for fluidity. Freezing time is based on the time at which a particular formulation appeared to be solidified. Formulations that appear to be solidified are removed to ambient temperature and allowed to thaw. Some samples that are frozen may re-solubilize when the temperature is brought to ambient conditions. Other samples that are frozen may remain as solid after elevating the temperature to ambient. The samples are kept at 0° C. for at least 14 days.

Results

Each of Examples 1-9 remains as a homogeneous solution after at least 14 days at 0° C. The stability test demonstrates that Examples 1-9 can maintain a homogeneous solution at 0° C. for at least 14 days.

In one comparison study, it is found that although a homogeneous solution of NBPT with a concentration over 50% by weight can be prepared at room temperature, the solution either freezes rapidly within a few hours or has crystals precipitate out from the solution within 1-4 days at 0° C.

In another comparison study, it is found that if the amount of dye used is over 2% by weight, the whole solution becomes frozen overnight at 0° C.

In another comparison study, a less pure NBPT (about 78% purity) obtained from Wipe Film Evaporator was used to make solutions with essentially the same method as Example 1. All tested solutions froze at 0° C. from day 1 to day 6.

In a further comparison study, it is found that if the ratio of NMP to PG is lower than 1, almost the whole solution becomes solid, even when the NBPT concentration is about only 30% by weight and the dye concentration is only 0.67% by weight, i.e. AGROTAIN® ULTRA (see http://www.kochfertilizer.com/pdf/kas_agroultra_na_en_20111006.pdf; http://ekova.com/download/product-information/Agrotain_Ultra/Agrotain%20ultra%20Label.pdf). This demonstrates that more NMP than propylene glycol may be required to achieve a low temperature resistant highly concentrated NBPT solution.

We claim:

1. A highly concentrated phosphoric or thiophosphoric triamide composition comprising:

i). a phosphoric or thiophosphoric triamide with a concentration range from 35% to 50% by weight, wherein said phosphoric or thiophosphoric triamide is a compound according to Formula I:

(X=P)(NH$_2$)$_2$NR$^1$R$^2$     (Formula I)

wherein X is oxygen or sulfur, and R$^1$ and R$^2$ are independently hydrogen, C$_1$-C$_{12}$ alkyl, C$_3$-C$_{12}$ cycloalkyl, C$_6$-C$_{14}$ aryl, C$_2$-C$_{12}$ alkenyl, C$_2$-C$_{12}$ alkynyl, C$_5$-C$_{14}$heteroaryl, C$_1$-C$_{14}$ heteroalkyl, C$_2$-C$_{14}$ heteroalkenyl, C$_2$-C$_{14}$ heteroalkynyl, or C$_3$-C$_{12}$ cycloheteroalkyl;

ii). a glycol or glycol derivative with a concentration range from about 5% to about 30% by weight, wherein said glycol is a compound according to C$_n$H$_{2n}$(OH)$_2$ (Formula II), and wherein n is 2-12; and iii). a liquid amide with a concentration range from about 20% to about 50% by weight, wherein said liquid amide is selected from the group consisting of 2-pyrrolidone, N—(C$_1$-C$_{12}$ alkyl)-2-pyrrolidone, and an amide with the formula R$^1$CONR$^2$R$^3$, wherein R$^1$ is a hydrogen or C$_1$-C$_4$ alkyl, and R$_2$ and R$_3$ are independently hydrogen or C$_1$-C$_{12}$ alkyl, wherein the ratio of the weight percentage of iii) to ii) is more than 1.0, and wherein said highly concentrated phosphoric or thiophosphoric triamide composition is physically stable at a temperature of 0° C., and there is substantially no freezing of the composition or crystallization of any solid for at least 14 days at 0° C.

2. The highly concentrated phosphoric or thiophosphoric triamide composition according to claim 1, further comprising a dye with a concentration range from about 1.0% to about 2.0% by weight.

3. The highly concentrated phosphoric or thiophosphoric triamide composition according to claim 1, wherein said phosphoric or thiophosphoric triamide is N-(n-butyl) thiophosphoric triamide (NBPT).

4. The highly concentrated phosphoric or thiophosphoric triamide composition according to claim 1, wherein said glycol or glycol derivative is a compound according to Formula II, and wherein n is 2-6.

5. The highly concentrated phosphoric or thiophosphoric triamide composition according to claim 1, wherein said glycol or glycol derivative is propylene glycol (PG).

6. The highly concentrated phosphoric or thiophosphoric triamide composition according to claim 1, wherein said liquid amide is N—(C$_1$-C$_{12}$ alkyl)-2-pyrrolidone.

7. The highly concentrated phosphoric or thiophosphoric triamide composition according to claim 1, wherein said liquid amide is N-methyl-2-pyrrolidone (NMP).

8. The highly concentrated phosphoric or thiophosphoric triamide composition according to claim 1, comprising:
  i). N-(n-butyl) thiophosphoric triamide (NBPT) with a concentration in the range from about 42% to about 48% by weight;
  ii). propylene glycol (PG) with a concentration in the range from about 8% to about 15% by weight;
  iii). N-methyl-2-pyrrolidone (NMP) with a concentration in the range from about 35% to about 45% by weight; and
  iv). a dye with a concentration in the range from about 1.2% to about 1.8% by weight.

9. A method comprising contacting a composition according to claim 1 with a urea-based fertilizer.

10. The method according to claim 9, wherein said urea-based fertilizer is urea granules or prills.

11. The method according to claim 9, wherein said urea-based fertilizer is molten urea.

12. A urea-based fertilizer comprising urea and a highly concentrated phosphoric or thiophosphoric triamide composition according to claim 1.

13. A method of making the highly concentrated NBPT composition according to claim 1 by combining NBPT, PG, NMP and a dye to make a homogeneous solution.

\* \* \* \* \*